(12) United States Patent
Brand (10) Patent No.: US 9,251,302 B2
(45) Date of Patent: Feb. 2, 2016

(54) SYSTEM AND METHOD FOR PLANNING A RADIATION THERAPY TREATMENT

(71) Applicant: Mitsubishi Electric Research Laboratories, Inc., Cambridge, MA (US)

(72) Inventor: Matthew Brand, Newton, MA (US)

(73) Assignee: Mitsubishi Electric Research Laboratories, Inc., Cambridge, MA (US)

(*) Notice: Subject to any disclaimer, the term of this patent is extended or adjusted under 35 U.S.C. 154(b) by 199 days.

(21) Appl. No.: 14/154,725

(22) Filed: Jan. 14, 2014

(65) Prior Publication Data

US 2015/0199457 A1 Jul. 16, 2015

(51) Int. Cl.
*A61N 5/00* (2006.01)
*A61N 5/10* (2006.01)
*G06F 17/10* (2006.01)
*G06F 17/50* (2006.01)

(52) U.S. Cl.
CPC ............ *G06F 17/5009* (2013.01); *G06F 17/10* (2013.01)

(58) Field of Classification Search
CPC ....... A61N 5/1031; A61N 5/103; A61N 5/00; A61N 5/10; A61N 5/1043; A61N 5/1064; G06F 17/10
USPC .............................................. 378/65, 64, 901
See application file for complete search history.

(56) References Cited

U.S. PATENT DOCUMENTS

| | | | | |
|---|---|---|---|---|
| 6,714,620 B2* | 3/2004 | Caflisch | A61N 5/103 | 378/65 |
| 6,792,073 B2* | 9/2004 | Deasy | A61N 5/1031 | 378/64 |
| 7,496,173 B2* | 2/2009 | Goldman | A61N 5/1031 | 378/65 |
| 7,529,339 B2* | 5/2009 | Goldman | A61N 5/1031 | 378/65 |
| 7,804,935 B2* | 9/2010 | Yin | A61N 5/1031 | 378/65 |
| 7,945,022 B2* | 5/2011 | Nelms | A61N 5/1071 | 378/65 |
| 8,325,878 B2* | 12/2012 | McNutt | A61N 5/1031 | 378/65 |
| 8,403,821 B2* | 3/2013 | Handa | A61N 5/1049 | 378/65 |
| 8,422,631 B2* | 4/2013 | Takahashi | A61N 5/103 | 378/65 |
| 8,682,414 B2* | 3/2014 | Nishimoto | A61N 5/103 | 378/62 |
| 2002/0027971 A1* | 3/2002 | Deasy | A61N 5/1031 | 378/65 |
| 2006/0259282 A1* | 11/2006 | Failla | A61N 5/1031 | 703/2 |
| 2012/0041685 A1 | 2/2012 | Ding et al. | | |
| 2013/0102830 A1* | 4/2013 | Otto | A61N 5/1031 | 600/1 |
| 2015/0038762 A1* | 2/2015 | Bert | A61N 5/1031 | 600/1 |
| 2015/0199457 A1* | 7/2015 | Brand | G06F 17/10 | 703/2 |
| 2015/0202464 A1* | 7/2015 | Brand | A61N 5/103 | 600/1 |

OTHER PUBLICATIONS

Mihaylov et al. "Analytic IMRT dose calculations utilizing Monte Carlo to predict MLC fluence modulation," NIHPA, Med Phys. Apr. 2006: 33 (4): 828-839.

* cited by examiner

*Primary Examiner* — David A Vanore
(74) *Attorney, Agent, or Firm* — Dirk Brinkman; Gene Vinokur (57) ABSTRACT

A method for planning a radiation therapy treatment of a body represented by a volume of voxels determines a radiation dose matrix representing a spatial distribution of a radiation dose of beams of radiation irradiating the volume with homogeneous stopping power. The beams are collimated and are shifted copies of each other at each depth of the volume, and the spatial distribution is determined by calculating cumulative beam-axial doses in a single matrix-matrix multiplication and redistributing the cumulative beam-axial doses to all voxels in the volume using a convolution. Next, a set of correcting operations is applied to the radiation dose matrix to produce a cumulative voxel radiation dose of the volume. Each correcting operation is linear, independent from another correcting operation and has a transform.

12 Claims, 9 Drawing Sheets

SYSTEM AND METHOD FOR PLANNING A RADIATION THERAPY TREATMENT

FIELD OF THE INVENTION

This invention relates generally to radiation therapy treatment planning, and particularly to determining a radiation dose for the radiation therapy.

BACKGROUND OF THE INVENTION

Radiation therapy is used to treat malignant tissue, such as cancer cells. The radiation can have an electromagnetic form, such as high-energy photons, or a particulate form, such as an electron, proton, neutron, or alpha particles.

Fast and accurate dose determination is important for radiation therapy treatment planning to ensure that the correct dose is delivered to a specific patient. Dose determination generally includes two parts: a source model and a transport model. The source model provides the incident fluence, which is the flux of the radiation integrated over time. The transport model determines the dose that results from the incident fluence. In conventional treatment planning system the transport model is a performance bottleneck. The three main transport methods in an order of increasing accuracy or decreasing performance are pencil beam, superposition and convolution, and Monte Carlo simulation. Superposition and convolution is the most common method for determining the radiation dose for external beam radiation therapy.

In particle beam radiation therapy treatment, a tissue volume is irradiated by a large number of directed pencil beams of radiation at various depths. Typically, the treatment planning volume, which represents a region within the patient, is partitioned into a rectangular 3D grid of voxels. To validate a treatment plan, it is necessary to determine the irradiation pattern of tens of thousands of beams for millions of voxels in the volume. To optimize a dose plan, it is necessary to determine the adjoint of this operation.

The radiation pattern can be modeled as a spatial distribution of radiation deposited by each beam. The relative intensity of radiation delivered to the $i^{th}$ voxel by the $j^{th}$ beam is represented by a positive number $A^{ij}$ and the table of numbers for all such beams and voxels is called a fluence matrix $A \in R^{V \times P}$, wherein V is a number of voxels and P is a number of pencil beams. In present-day treatment settings there may be $V \geq 10^6$ voxels and $P \approx 10^5$ pencil beams, resulting in a fluence matrix of $8V P \approx 10^{12}$ bytes. This is too large to be stored in conventional memories, or used even in most supercomputers. Thus, the direct determination of the fluence matrix A is currently impractical.

Some dose calculation methods determine a cumulative voxel radiation dose applied during the treatment without explicitly constructing the fluence matrix. Some conventional methods determine the cumulative voxel radiation dose via Monte Carlo simulation or via clinically validated approximations. For example, one method calculate the contributions of the pencil-beams one at a time, e.g., by ray-tracing 3D dose distribution each pencil beam, and accumulate the result into a 3D array representing the cumulative doses to all voxels, see U.S. Pat. No. 8,325,878.

Some state-of-the-art dose optimization techniques use a sparse approximation of the fluence matrix, in which a subset of fluence values above a predetermined threshold are stored, and the remaining small fluence values are neglected. However, such a sparse enough matrix that can be stored in a computer memory disregards about 1-4% of the total radiation.

In addition, the conventional methods are not fast enough for a real time dose calculation. Further, those methods are not suitable to determine the action of the adjoint $A^T$ of the fluence matrix, which can be necessary to determine the gradient of the error in various dose optimization techniques.

SUMMARY OF THE INVENTION

Some embodiments of invention are based on a realization that there is no need to directly approximate or accumulate an accurate cumulative voxel radiation dose suitable for clinical use. Instead, it is advantageous to efficiently determine an initial approximation of the cumulative voxel radiation dose that is inaccurate and may not be suitable for t clinical use, and then subsequently correct the initial approximation with a set of independent operations having an adjoint.

The approximation can be decomposed into independent operations to allow efficient calculation using multiple parallel processors. Because the correcting operations are also decomposable, the initial approximation can be subsequently corrected. Because each operation has a transpose, the transpose can be applied to the cumulative voxel radiation dose in a reverse order to obtain quantities needed for the dose optimization, such as the gradient of the dose error with respect to beam weights.

It was realized and proved that approximation and the subsequent corrections are independent, linear operations that can be implemented in parallel and can make extensive use of graphic processor units (GPU). Overall, various embodiments determine can increase the determination of the cumulative voxel radiation dose in one or two orders of magnitude.

Accordingly, one embodiment of the invention discloses a method for planning a radiation therapy treatment of a body represented by a volume of voxels. The method includes determining a radiation dose matrix representing a spatial distribution of a radiation dose of beams of radiation irradiating the volume with homogeneous stopping power, wherein the beams are collimated and are shifted copies of each other at each depth of the volume, wherein the spatial distribution is determined by calculating cumulative beam-axial doses in a single matrix-matrix multiplication and redistributing the cumulative beam-axial doses to all voxels in the volume using a convolution; and applying a set of correcting operations to the radiation dose matrix to produce a cumulative voxel radiation dose of the volume, wherein each correcting operation is linear, independent from another correcting operation and has a transform. The steps of the method are performed by at least one processor.

Another embodiment discloses a method for planning a radiation therapy treatment of a body represented by a volume of voxels including determining a radiation dose matrix representing a spatial distribution of a radiation dose of a regular 3D grid of beams irradiating the volume with homogeneous stopping power; and applying a set of correcting operations to the radiation dose matrix to produce a cumulative voxel radiation dose of the volume. The set of correcting operation includes one or combination of an operation for correcting an assumption of uniformity of lateral distribution of energy of each collimated beam, an operation for correcting an assumption of the homogeneous stopping power of the volume, an operation for correcting an assumption of a parallel distribution of the collimated beams, an operation for correcting an assumption of a multi-port propagation of the collimated beams, and an operation for correcting an assumption for a cumulative stopping power of media between a beam source and the patient, wherein each correcting operation is linear, independent from another correcting operation and has a transform. The steps of the method are performed by a parallel processor.

Yet another embodiment discloses a radiation therapy system comprising a parallel processor for determining an approximation of a radiation dose matrix representing a spatial distribution of a radiation dose of beams of radiation irradiating a body represented by a volume of voxels, wherein the spatial distribution is determined by calculating cumulative beam-axial doses in a single matrix-matrix multiplication and redistributing the cumulative beam-axial doses to all voxels in the volume using a convolution, and for correcting the approximation using a set of linear correcting operations.

DETAILED DESCRIPTION OF THE PREFERRED EMBODIMENTS

Figure 1:
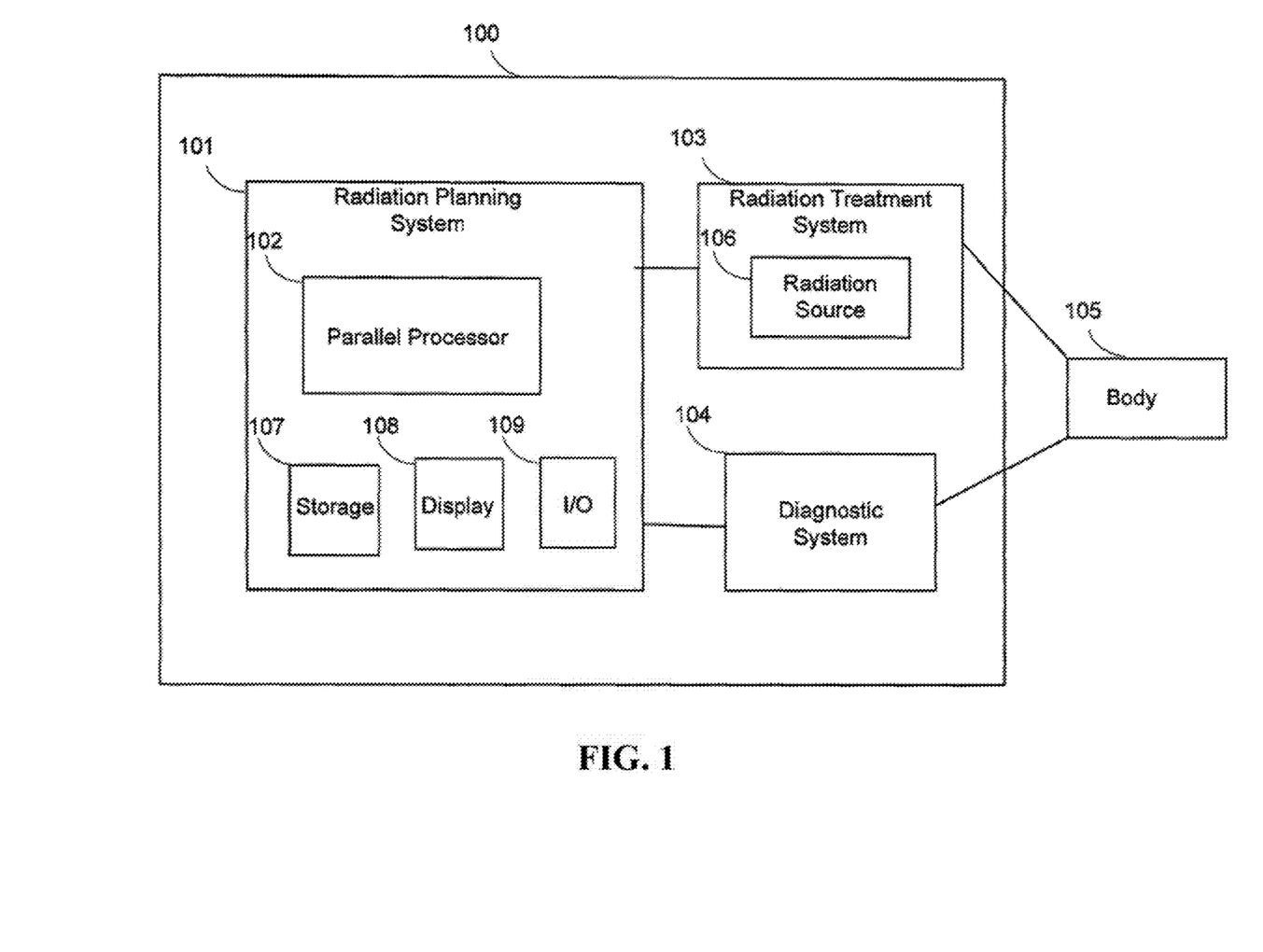
FIG. 1 is a schematic diagram of a radiation therapy system 100 according to one embodiment of the invention.

FIG. 1 is a schematic diagram of a radiation therapy system 100 according to one embodiment of the invention. The radiation therapy system 100 includes a radiation treatment planning system 101, which further includes a parallel processor 102. The parallel processor is adapted to receive input information concerning a body 105 having an intended radiation treatment volume that can be represented as a volume of voxels. The parallel processor 102 is also adapted to generate output information for providing radiation treatment to the intended radiation treatment volume of the body.

The radiation treatment planning system 101 can further include a storage 107, a display 108, and input/output (I/O) devices and interfaces 109. The storage 107 may be, for example, a hard disk drive, a CD-ROM drive, a DVD drive, a flash drive, etc. The display 108 may be, for example, a liquid crystal display (LCD), a cathode ray tube (CRT) monitor, a plasma display, etc. I/O device 109 may include, for example, a mouse, a keyboard, an interface for data transfer over a network or a data bus.

The radiation therapy system 100 can further include a radiation treatment system 103 that is in communication with the radiation treatment planning system 101. The radiation treatment system 103 can include a radiation source 106 that emits a directed beam of radiation for treatment. Examples of radiation sources may include, a X-ray source, a gamma ray source, an electron beam source, etc. The radiation source 106 may further comprise a multi-leaf collimator (MLC) to shape the beam. By adjusting the position of the leaves of the MLC, a radiotherapist can match the radiation field to a shape of the treatment volume of body. Other beam shaping and/or contouring can be included in some embodiments. The radiation source 106 can have a corresponding source model. The radiation system 103 may be controlled by the radiation treatment planning system 101, for example, to deliver intensity modulated radiation energy and to conform radiation treatment to the shape of the intended radiation treatment volume.

The radiation therapy system 100 can also include a diagnostic system 104, in communication with the radiation treatment planning system 101 that generates empirical data of body 105, e.g., a body of a human. The empirical data may be used as input information to the radiation treatment planning system 101 and the parallel processor 102 and may be used to determine the dose of radiation. The diagnostic system 104 can include sensors to obtain the empirical data of body 105. An example diagnostic system may be a computed tomography (CT) scanner, a magnetic resonance imaging (MRI) scanner, a positron emission tomography (PET) scanner.

Some embodiments of the invention are based on a recognition that for particle beam dose calculation and optimization, it is necessary to rapidly determine cumulative voxel radiation dose using a matrix-vector products Aw and/or $A^T \lambda$, without explicitly constructing the matrix A, wherein T is the transpose operator, w is a vector of nonnegative beam weights and $\lambda$ is a vector of errors in the doses of the voxels.

Figure 2:
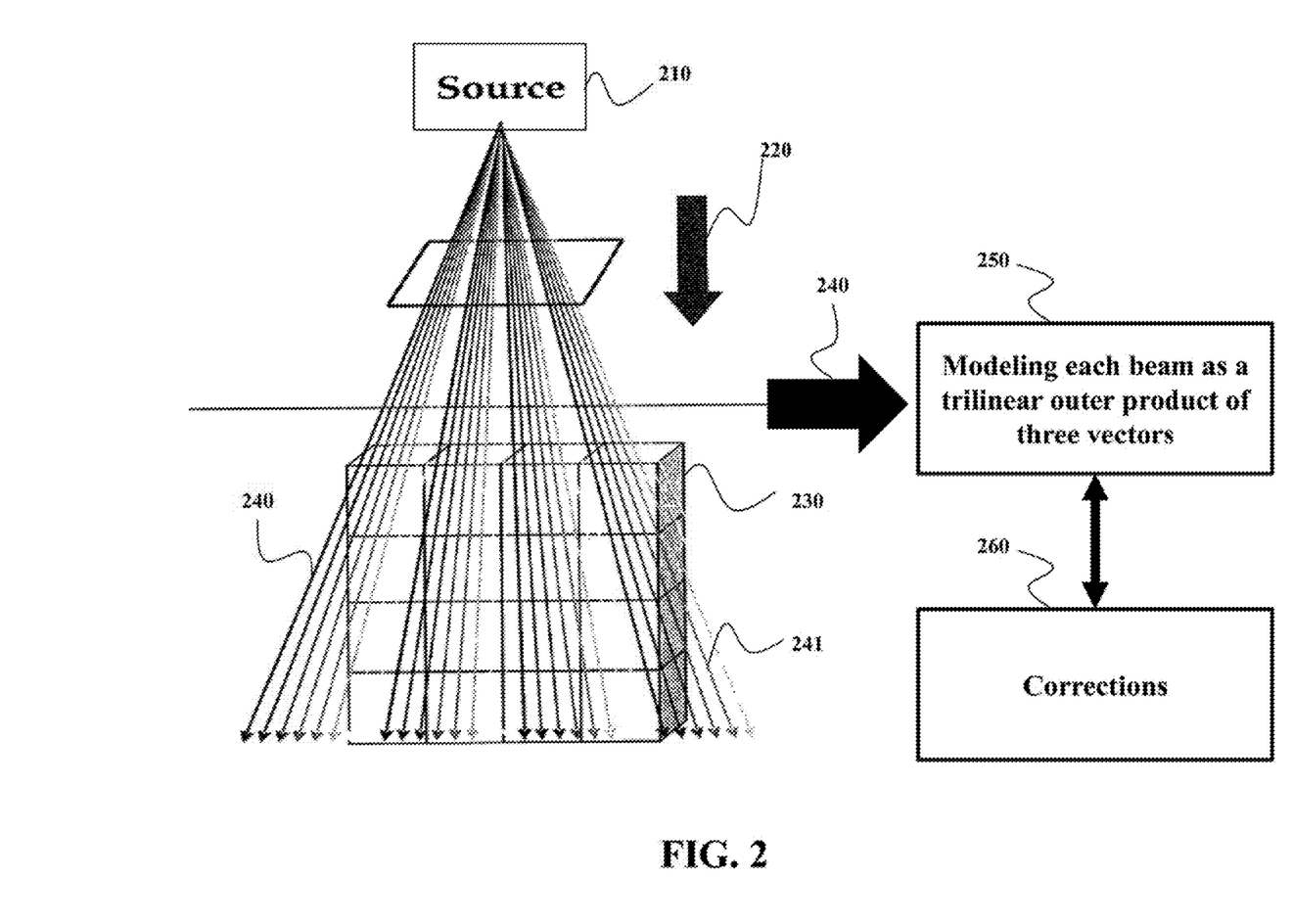
FIG. 2 is a schematic of a principle employed by some embodiments of the invention.

FIG. 2 shows a schematic of a principle employed by some embodiments of the invention. In particle beam treatment, a volume 230 of a body of a patient is irradiated 220 by a large number of pencil beams, e.g., the beams 240-241, that are directed at different points in the patient, and penetrate to different depths. In a first order approximation, the beams can be considered as translated copies of each other, and the 3D irradiation field of each beam can be modeled 240 as a trilinear outer product 250 of three vectors. The trilinear outer product can be used to rapidly approximate a linear superposition of many parallel beams directed at a rectangular grid of targets.

Furthermore, some embodiments determine the trilinear outer product by calculating cumulative beam-axial doses in a single matrix-matrix multiplication and redistributing the doses to all voxels in the volume of the patient in a convolution, as described in more details below. Such calculations further increase the efficiency of the computation.

However, this trilinear outer product ignores several phenomena and is too inaccurate for clinical use. For example, the beams of radiation aimed at different depths have different radiation profiles. Also, the irradiation pattern of each individual beam depends on the stopping and scattering power of the tissues the beam passes through. Similarly, the beams usually radiate from a common source 210 and propagation of each beam increases nonlinearly.

Some embodiments of the invention apply a sequence of corrections 260 to the dose approximation to account for all of these phenomena. Each of these correction operations has a transpose. By applying the transposes in a reverse order, some embodiments obtain quantities needed for dose optimization, such as the gradient of the dose error with respect to the beam weights.

Figure 3:
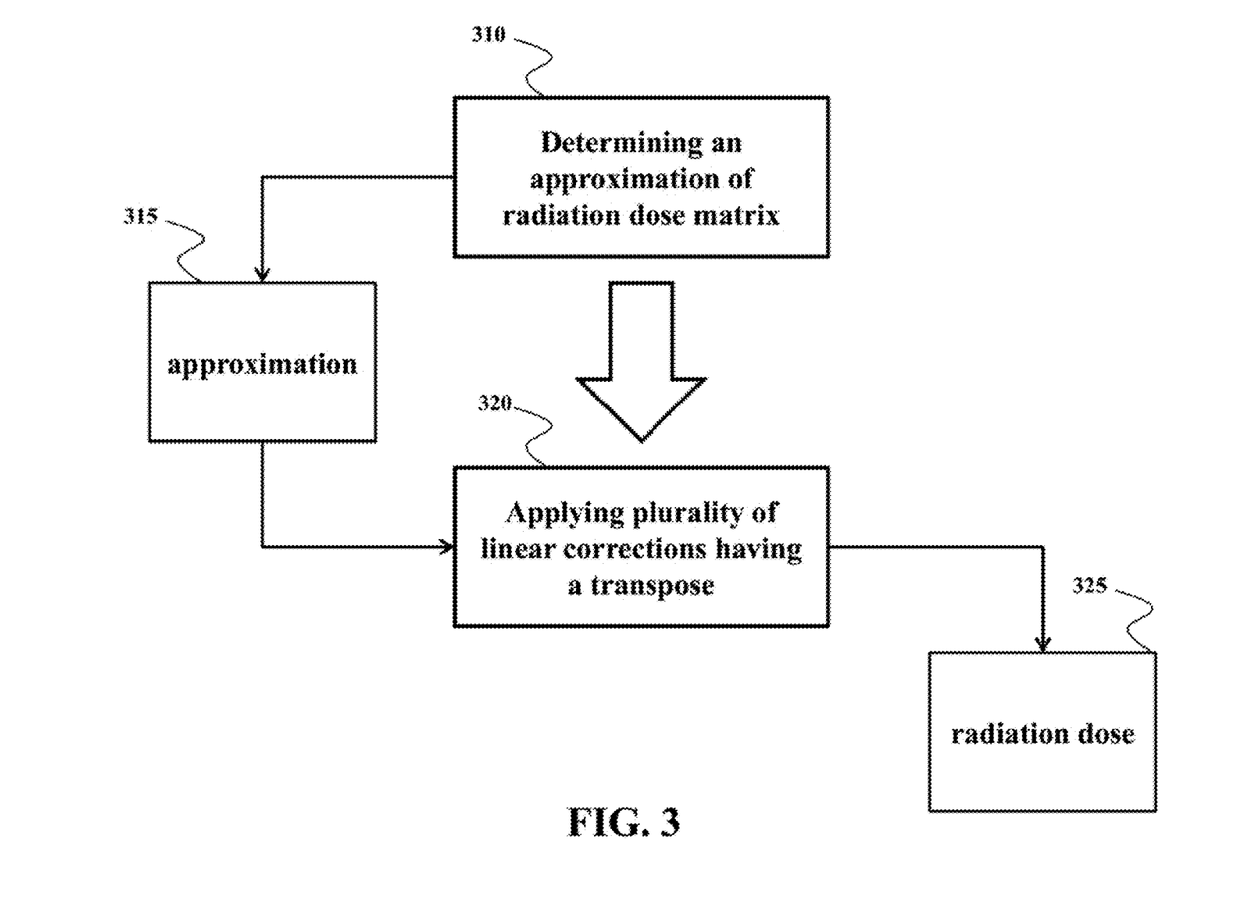
FIG. 3 is a block diagram of a method for radiation therapy treatment planning using beams of radiation irradiating a volume of a patient according to some embodiments of the invention.

FIG. 3 shows a block diagram of a method for radiation therapy treatment planning using beams of radiation irradiating a volume of a patient. The method determines a cumulative voxel radiation dose for the volume, and each step of the method can be implemented by the parallel processor 102.

Specifically, the method determines 310 a radiation dose matrix representing a spatial distribution of a radiation dose of a regular 3D grid of beams of radiation. The radiation dose matrix is approximated 315 based on the assumption that the beams are collimated, and collimated beams at each depth are shifted copies of each other for radiating the volume of the patient with homogeneous stopping power. Such an assumption allows for rapid determination of the approximation of the radiation dose on the parallel processor.

Next, the method applies 320 a set of correcting operations to the radiation dose matrix to produce a cumulative voxel radiation dose 325 of the volume. Each correcting operation is linear, independent from another correcting operation, and has a transpose.

Rapid Dose Calculation Using Outer Products

Some embodiments approximate a spatial distribution of a radiation dose based on assumption that all beams are of a given energy and are grid-translated copies of a single beam. For each beam, the density of energy deposition by the beam (as a function of depth z) is presumed to follow some energy profile, e.g., a Bragg profile $B(z)$. Also, the dispersion of energy transverse to the beam is assumed to follow some distribution $D(x, y, z)$, so that the cumulative energy deposited in some voxel of width $\Delta$ centered on a location $(x_0, y_0, z_0)$ is $$E(x_0,y_0,z_0,\Delta) = \int_{z_0-\Delta/2}^{z_0+\Delta/2} \int_{y_0-\Delta/2}^{y_0+\Delta/2} \int_{x_0-\Delta/2}^{x_0+\Delta/2} B(z) D(x,y,z) dx dy dz.$$

Further, the 2D lateral distribution of the dose is assumed to be independent of depth z and separable into two i.i.d. (independently and identically distributed) 1D distributions, usually Gaussian profiles, so that $D(x, y, z) = N(x)N(y)$ and $$E_{sep}(x_0,y_0,z_0,\Delta) = \int_{z_0-\Delta/2}^{z_0+\Delta/2} \int_{yz-\Delta/2}^{y_0+\Delta/2} \int_{x_0-\Delta/2}^{x_0+\Delta/2} B(z) N(x) N(y) dx dy dz.$$

It is assumed that the voxels are small enough that the distribution functions are approximately linear within the voxel, so the integral is essentially trilinear, and, thus, can be approximated by either of these outer products:

$$\lim_{\Delta \to 0} E_{sep}(x_0, y_0, z_0, \Delta) =$$

$$\left(\int_{z_0-\Delta/2}^{z_0+\Delta/2} B(z) dz\right)\left(\int_{yz-\Delta/2}^{y_0+\Delta/2} N(y) dy\right)\left(\int_{x_0-\Delta/2}^{x_0+\Delta/2} N(x) dx\right)$$

or $$\lim_{\Delta \to 0} E_{sep}(x_0, y_0, z_0, \Delta) = \Delta^3 B(z_0) N(x_0) N(y_0)$$

This approximation enables a fast "outer product" procedure to determine the weighted sum of all beams that includes one small matrix-matrix multiplication and (hardware-accelerable) 1D or 2D convolution(s).

Figure 4:
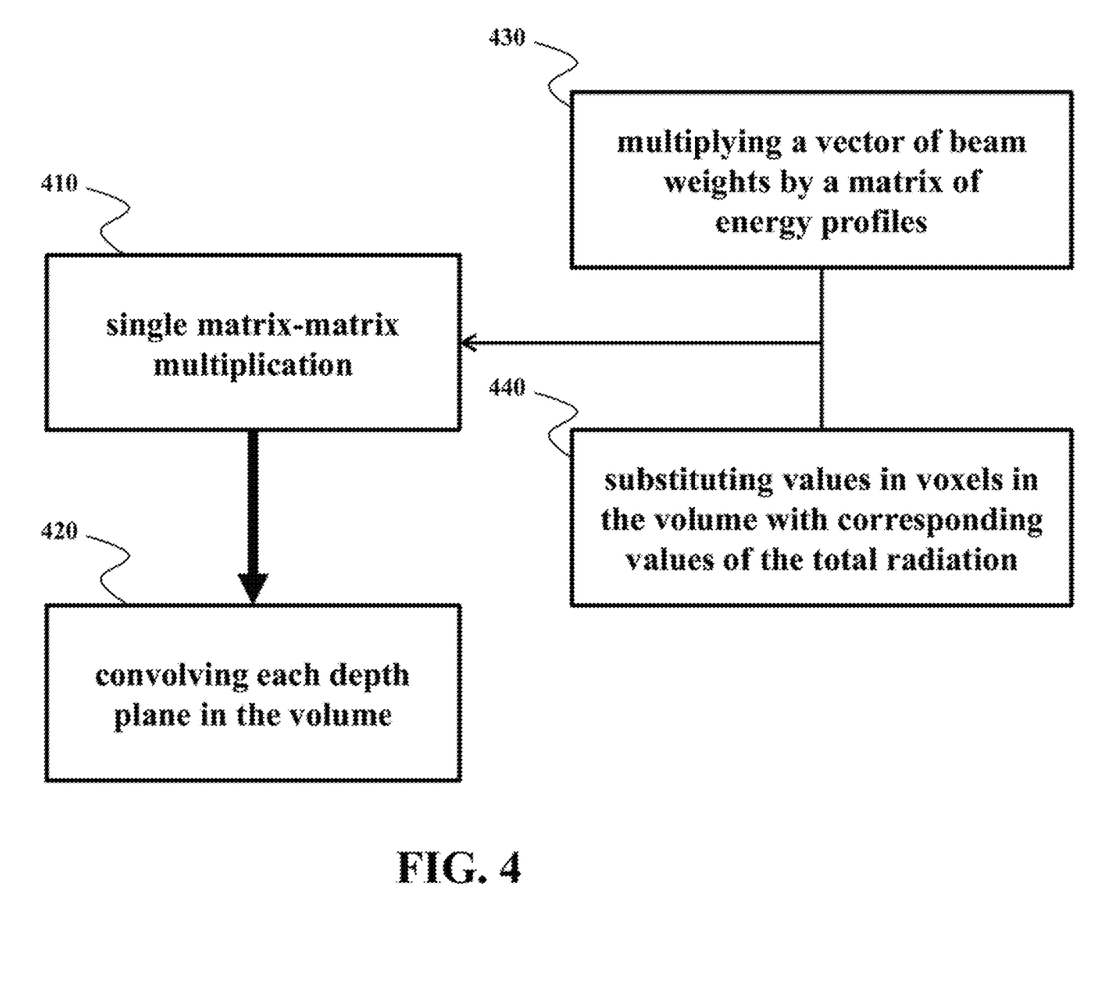
FIG. 4 is a block diagram of a method for determining an approximation of the spatial distribution of the radiation dose according to one embodiment.

FIG. 4 shows a block diagram of a method for determining the approximation of the spatial distribution of the radiation dose according to one embodiment. In that embodiment, the spatial distribution is determined by calculating cumulative beam-axial doses in a single matrix-matrix multiplication 410 and redistributing the doses to all voxels in the volume of the patient in a convolution 420.

In particular, in discretizing to computer-representable voxel doses, let N be a column vector containing the values of the lateral distribution (e.g., a 1D Gaussian density function) and let N be a matrix in which each column is a spatially shifted copy of N, the shift matching the lateral spacing between beams. Similarly, let B be a vector containing the values of a Bragg profile and let B be a matrix of spatially shifted Bragg profiles (or let each column in B contain a unique energy profile for all beams in one energy layer). Then the shared outer product structure of all beams can be summarized by the formula vec (A)=vec (N⊗ N⊗ B), where ⊗ is the Kronecker matrix product and where vec (•) vectorizes its argument.

To use this in a method for dose calculation, one embodiment twice apply the matrix equality vec (UXV)=($V^T$⊗ U) vec (X), obtaining $$Aw = \text{vec}(B^T \text{mat}(w)(N \otimes N))$$

where mat (•) reshapes its argument into a matrix that conforms to its left and right multiplicands.

This enables is a very efficient mechanism to obtain the dose deposition Aw by multiplying 430 a vector of beam weights by a matrix of energy profiles, e.g., as a product $B^T$ mat (w). Each value in $B^T$ mat (w) is the cumulative radiation deposited into a specific Z plane by all beams that center on a specific X,Y coordinate. To calculate the dose, one embodiment substitute 440 values in voxels in the volume with corresponding values of the total radiation, i.e., arrange these values at their XYZ coordinates in a 3D array otherwise filled with zeroes, and then convolves 420 the volume with a 2D (XY) lateral spreading kernel.

If the kernel itself is separable into the outer product of two 1D kernels (as is the case for Gaussian kernels), then a 2D convolution can be replaced with two 1D convolutions. For example, the convolving includes a first convolution with a first vector in a first lateral direction, followed by a second convolution with a second vector in a second lateral direction orthogonal to the first lateral direction, e.g., one convolution is in X direction followed by the convolution in Y direction. Both the matrix-vector product and the convolutions can be natively parallelized by a graphics processor unit (GPU).

An equivalent method for computing the transpose $A^T \lambda$ begins with the observation that $A^T = N^T \otimes N^T \otimes B^T$, and then proceeds using the same arguments. Because the Kronecker factors are reversed, the method for computing the transpose $A^T \lambda$ is also reversed. For example, one embodiment places values in $\lambda$ in the 3D grid, 2D-convolve the 3D grid and then extract the values along the beam axes and place those values in a matrix which is multiplied on the left by B to yield $A^T \lambda$.

Correcting Operations

The approximation can be decomposed into independent operations to allow efficient calculation using multiple processors. Because the correcting operations are also decomposable, the initial approximation can be subsequently corrected in parallel with the help of multiple processors. Because each operation has a transpose, the transpose can be applied to the cumulative voxel radiation dose in reverse order to obtain quantities needed for the dose optimization, such as the gradient of the dose error with respect to the beam weights. However, the trilinear approximation of the cumulative voxel radiation dose is inaccurate based on one or combination of the following.

First, the approximation assumes that transverse slices of all beams have identical, e.g., Gaussian, lateral distributions at all depths. In practice, the variance of the lateral distribution increases nonlinearly with increasing depth in the patient, so that beam has a unique dilation at each depth. Some embodiments of the invention are based on a realization that the inaccuracy of the approximation due to unmodelled lateral variance can be reduced by convolving different depth planes in the 3D array with different lateral spread kernel(s).

Notably, such a convolution can be performed in parallel using multiple processors and has an adjoint operation.

Second, the approximation assumes irradiation of the volume with a homogeneous stopping power, e.g., water. In practice, the tissues in the volume of the patient are inhomogeneous, i.e., voxels representing bones have a relatively high radiation stopping power, while voxels representing air have very little stopping power.

Some embodiments of the invention are based on a realization that the inaccuracy of the approximation due to the variance of the stopping power in the volume can be reduced by stretching and contracting the voxels in the original homogeneous volume along the line of the propagation of the beam until the length of each voxel is inversely proportioned to its stopping power. For example, if the approximation of the cumulative voxel radiation dose is determined for the volume of water, a bone in the volume effectively shortens the beam, while the air effectively lengthens the beam. With such stretching and contracting operations, the dose deposition at the usual linear rate delivers the correct dose to each voxel.

Because such stretching and contracting is computationally complex and incompatible with the original trilinear approximation, embodiments based on this realization account for inhomogeneous tissues by making corrections to the cumulative dose deposited in a homogeneous volume based on a redistribution matrix R that linearly maps irradiation values from those deposited into regular grid into those that would be deposited into a stretched grid. Notably, the redistribution matrix can be predetermined, e.g., based on Hounsfield radiodensity values associated with computer-aided tomography density readings of the patient. The application of the redistribution matrix can also be performed in parallel using multiple processors and has an adjoint operation.

Third, the approximation assumes irradiation of the volume with parallel beams. In practice, the beams can radiate from a common focal point. Some embodiments are based on a recognition that a Euclidean space can be warped so that all lines parallel to one axis meet at a focal point. Similarly, there is a counter-warp that inverts this warp (except at the focal point, which is a singularity). Thus, some embodiments counter-warp the patient geometry and tissue density data. Then, dose deposition and redistribution proceeds as described above. Then, the planning volume is warped back to its original geometry. Once again, the warp and counter-warp are linear operators that can be handled by parallel computing operations or represented by a very sparse matrix that can be combined (or sequenced) with the rotation and heterogeneous tissue redistribution matrices.

The warp and counter-warp operations change the volume of any subvolume but do not change the stopping power or cumulative radiation in that subvolume. In addition, the counter-warp can also be applied to the beam-spreading profiles to keep the geometry of the beams consistent with the geometry of the treatment volume.

Fourth, the volume between the source of radiation and the body of the patient has to be considered.

Figure 5:
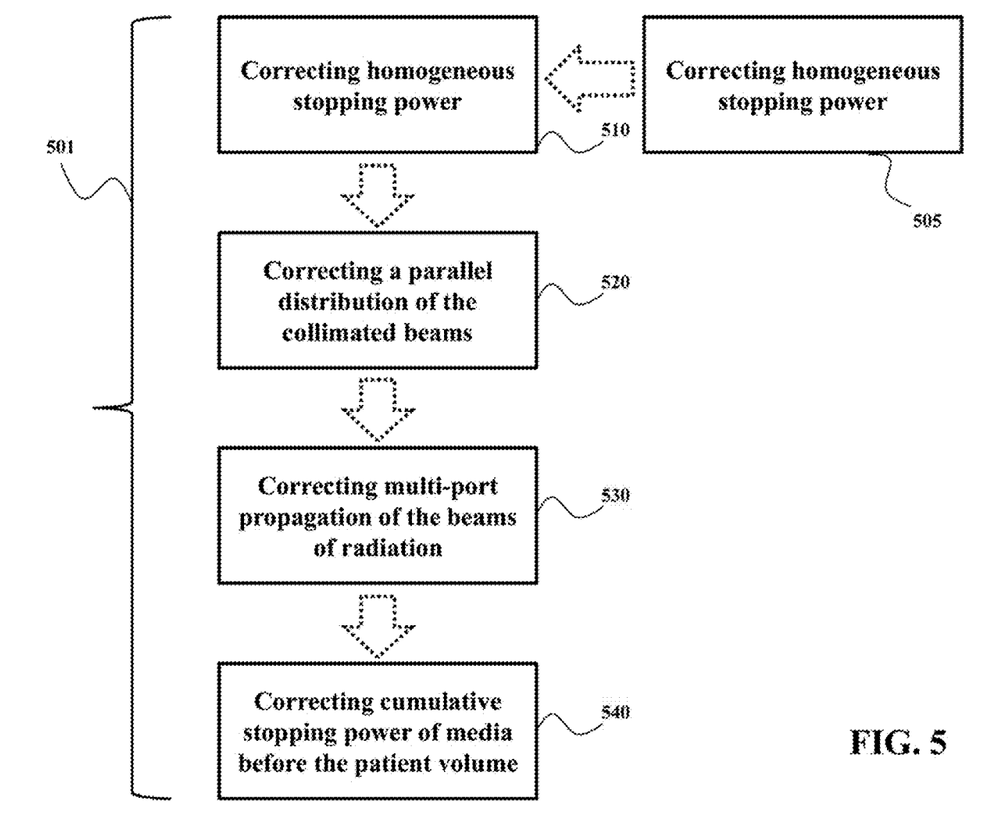
FIG. 5 is a schematic showing a set of correcting operations used by some embodiment of the invention to correct inaccuracy of initial approximation.

FIG. 5 shows a schematic of a set of correcting operations 501 used by some embodiment of the invention to correct inaccuracy of the approximation 315. The set of correcting operations 510 includes one or combination of an operation for correcting an assumption of uniformity of lateral distribution of energy of each collimated beam 505, an operation for correcting an assumption of the homogeneous stopping power of the volume 510, an operation for correcting an assumption of a parallel distribution of the collimated beams 520, an operation for correcting an assumption of a multi-port propagation of the collimated beams 530, and an operation for correcting an assumption for a cumulative stopping power of media between a beam nozzle and the patient volume 540.

Handling Variations in Lateral Beam Spread

The above convolution assumes that transverse slices of all beams have identical spreading distributions at all depths. In practice, the variance of the spreading distribution varies nonlinearly with depth, so that the beam has a unique dilation at each depth. That cannot be exactly accommodated in the outer product procedure, but it can be approximated very well, as follows.

Consider all beams with a shared axis (x, y). To sum their effects in voxel layer z, exactly, the sum is $$\Sigma_i w_i B_i(z) N((x,y), \sigma_i^2(z)), \quad (3.1)$$

where $w_i$ is the weight on the ith beam, $B_i(z)$ is the integral of the Bragg profile over the interval spanned by volume layer z, and $N((x,y), \sigma_i^2(z))$ is a 2D Gaussian field of variance $\sigma_i^2(z)$ centered at (x,y). Calculating and summing all these fields is very expensive. In the trilinear outer product procedure described above, all variances are presumed equal ($\forall_{i,z} \sigma_i^2(z) = \sigma^2$), and the sum is factored as $$(\Sigma_i w_i B_i(z)) \cdot N((x,y), \sigma^2). \quad (3.2)$$

One embodiment approximates the exact sum (eq. 3.1) with a weighted superposition of a small number of differently varianced and re-weighted outer products. I.e., the embodiment uses a small number J of basis fields $N((x\ y), \sigma_j^2(z))$, each with a pre-set variance $\sigma_j^2(z)$, $j=1 \ldots J$. This embodiment is based on a realization that for each basis, there is a function giving modified weights $u_{ij}(w_i B_i(z), \sigma_i^2(z), \sigma_j^2(z))$ and, thus, the exact sum can be approximated as $$\Sigma_j^J (\Sigma_i u_{ij}(w_i B_i(z), \sigma_i^2(z), \sigma_j^2(z))) \cdot N((x,y), \sigma_j^2(z)). \quad (3.3)$$

The new weighting function $u_{ij}(\bullet)$ can be obtained by solving a small and simple linear system of equations, as described below.

In particular, let minimize the weighted squared error of approximating a single 2D Gaussian field by a weighted sum of 2D Gaussian fields of different variances. For notational simplicity, assume that the target field is centered on the origin (0,0) with variance $\beta^2$, i.e., let minimize $$\left\| N((0,0), \beta^2) - \sum_j v_j N((0,0), \sigma_j^2) \right\|_2^2.$$

The embodiment determines the approximation to be most accurate near the beam core, and weights the squared error by another 2D Gaussian field $N((0,0), \alpha^2)$. The error is then $$E = \iint N((x,y);(0,0),\alpha^2) \cdot (N((x,y);(0,0),\beta^2) - \Sigma_j^J v_j N((x,y);(0,0),\sigma_j^2))^2 dx dy.$$

The error is convex, so to find the optimal weights $v_j$, the embodiment solves for the zeros of the partial derivatives $\partial_{v_j} E = 0$, obtaining a linear system $$\forall_j \left\{ \sum_k^J \frac{v_k}{\sigma_j^2 \sigma_k^2 + \alpha^2(\sigma_j^2 + \sigma_k^2)} = \frac{1}{\sigma_j^2 \beta^2 + \alpha^2(\sigma_j^2 + \beta^2)} \right\}$$

where each sum includes k=j.

The vector v of weights is given by the solution $$v = \begin{bmatrix} 1/(\sigma_1^2\sigma_1^2 + \alpha^2(\sigma_1^2 + \sigma_1^2)) & \cdots & 1/(\sigma_1^2\sigma_j^2 + \alpha^2(\sigma_1^2 + \sigma_j^2)) \\ \vdots & \ddots & \vdots \\ 1/(\sigma_j^2\sigma_1^2 + \alpha^2(\sigma_j^2 + \sigma_1^2)) & \cdots & 1/(\sigma_j^2\sigma_j^2 + \alpha^2(\sigma_j^2 + \sigma_j^2)) \end{bmatrix}^{-1} \quad (3.4)$$

$$\begin{bmatrix} 1/(\sigma_1^2\beta^2 + \alpha^2(\sigma_1^2 + \beta^2)) \\ \vdots \\ 1/(\sigma_j^2\beta^2 + \alpha^2(\sigma_j^2 + \beta^2)) \end{bmatrix}$$

If a uniform error weighting is desired, than $\alpha \to \infty$ and the linear system simplifies to $$\forall_j \left\{ \sum_k^j \frac{v_k}{\sigma_j^2 + \sigma_k^2} = \frac{1}{\sigma_j^2 + \beta^2} \right\}.$$

Thus, the vector v of weights is given by the solution $$v = \begin{bmatrix} 1/(\sigma_1^2 + \sigma_1^2) & \cdots & 1/(\sigma_1^2 + \sigma_j^2) \\ \vdots & \ddots & \vdots \\ 1/(\sigma_j^2 + \sigma_1^2) & \cdots & 1/(\sigma_j^2 + \sigma_j^2) \end{bmatrix}^{-1} \begin{bmatrix} 1/(\sigma_1^2 + \beta^2) \\ \cdots \\ 1/(\sigma_j^2 + \beta^2) \end{bmatrix} \quad (3.5)$$

It is possible that some $v_{ij}$ are negative; this does not affect the accuracy of the approximation but it can lead to so non-physical results. If that is not desired, the linear system can be replaced with the quadratic program $$\min_{\forall_k v_k \geq 0} \sum_k \left\{ \left( \sum_k^j \frac{v_k}{\sigma_j^2\sigma_i^2 + \alpha^2(\sigma_j^2 + \sigma_k^2)} \right) - \frac{1}{\sigma_j^2\beta^2 + \alpha^2(\sigma_j^2 + \beta^2)} \right\}^2.$$

In the larger dose calculation problem, the identification is $\beta^2 = \sigma_j^2(z)$, which licenses the factorization $u_{ij}(w_iB_i(z), \sigma_i^2(z), \sigma_j^2(z)) = v_{ij}(\sigma_i^2(z), \sigma_j^2(z)) \cdot w_iB_i(z)$, because now $v_{ij}$ only depends on the original variance $\sigma_i^2(z)$ and the basis set of approximating variances $\{\sigma_j^2(z)\}_j^J$ through equation (3.4). Writing out this dependence explicitly, the desired dilation-modeling superposition (eq. 3.3) becomes $$\Sigma_j^J \{(\Sigma_i v_{ij}(\sigma_i^2(z), \sigma_j^2(z)) \cdot w_iB_i(z)) \cdot N((x,y), \sigma_j^2(z)),\},$$

where each term in braces can be determined by the original outer product procedure. The approximation weights $v_{ij}$ can be pre-calculated (for every beam and z layer) and re-used for different beam weights $w_i$.

In one variation of the embodiment, where all the beams in one energy layer have the same dilation profile, the approximation weights depend only on the depth and the superposition further simplifies to a form that is close to the original trilinear approximation in eqn. 3.2, indicating that dilation across all beams can be modeled by summing a small number of trilinear approximations, each with different transverse spreads:

$$\Sigma_j^J (\Sigma_i w_i v_j(z) B_i(z)) \cdot N((x,y), \sigma_j^2). \quad (3.6)$$

Note that the dilation weights and the Bragg values can be premultiplied before any dose calculations yielding $\check{B}_i(z) \doteq v_j$ (z)$B_i(z)$, so that, procedurally, the embodiment only needs to sum over a few iterations of the original trilinear form:

$$\Sigma_j^J (\Sigma_i w_i \check{B}_i(z)) \cdot N((x,y), \sigma_j^2). \quad (3.7)$$

Numerical experiments indicate that J=4 fixed-variance Gaussian fields can be sufficient to give a high-quality approximation for all the transverse spreads encountered in typical dose optimization problems. For example, a weighted sum of 20 Gaussian fields with variances drawn randomly from the interval $\sigma_i(z) \in [3,6]$ mm can be approximated using a basis set of 4 Gaussian fields with fixed variances such that the maximum absolute error is less than 1/1000th of the exact peak value. The approximation can be made tighter by using more fields in the basis, or faster by using less. Notably, this correction operation uses a linear operator, i.e., its transpose is also available for dose optimization.

Dose Redistribution

In inhomogeneous tissues, voxels representing bone have a relatively high radiation stopping power, while voxels representing air have very little stopping power. To a first order, this can be modeled by stretching and contracting the voxels along the beam until they are inversely proportioned to their stopping power. Then, the dose deposition at the usual linear rate determines the correct dose for each voxel. Bone effectively shortens the beam; air effectively lengthens the beam. This "dose-volume equivalent" approximation usually requires serial ray-tracing of each beam progressing through the volume. The ray tracing can be accelerated using GPUs and reverse ray tracing techniques, but another two orders of magnitude speed-up is needed for real-time dose optimization. Furthermore, ray-tracing methods do not lend themselves to the gradient computation needed for dose optimization.

Figure 6:
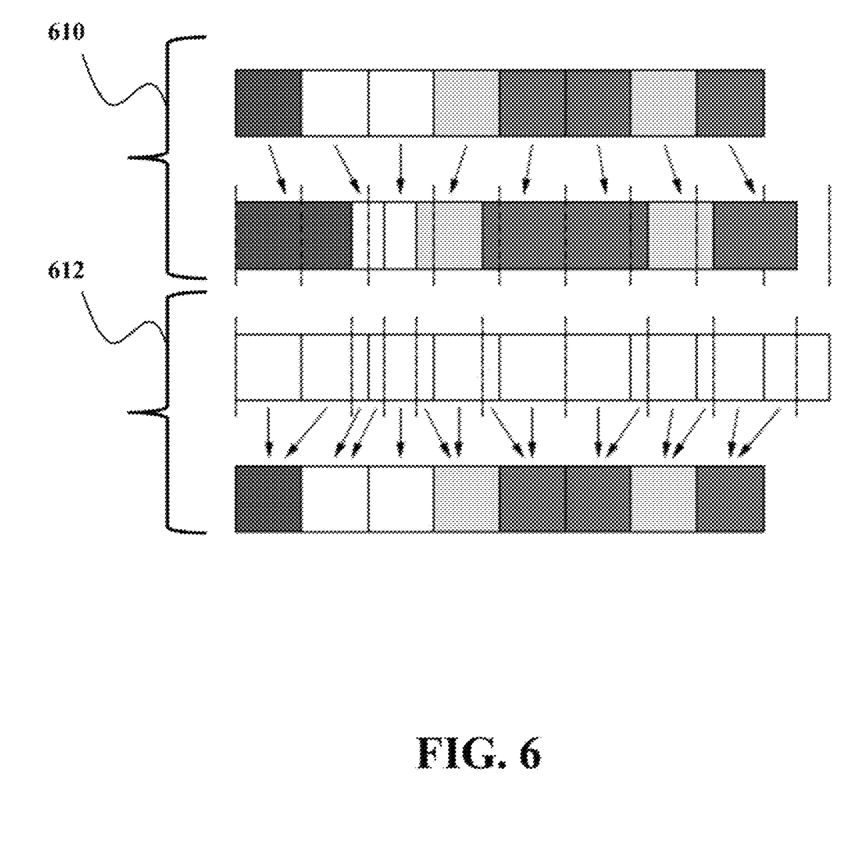
FIG. 6 is a schematic of a realization used by one embodiment of the invention.

FIG. 6 shows an illustration of a realization used by one embodiment of the invention. Specifically, instead of accounting for tissue inhomogeneity in the course of depositing the dose, it can be advantageous to account for such an inhomogeneity by making corrections to the dose after the dose has been deposited in a homogeneous volume. For example, in water-equivalent dosing 610, denser voxels are stretched to yield an irregular grid on which then radiation dosage is calculated. In redistribution dosing 612 employed by the embodiment, the radiation dosage is calculated on a regular grid and then redistributed to match the dosage pattern of the stretched voxels.

To model the effect of tissue inhomogeneity on radiation deposition, one embodiment uses a perturbational procedure that is amenable to massively parallel computation. The embodiment precalculates a redistribution matrix R that linearly maps irradiation values from those deposited into regular grid into those that would be deposited into a stretched grid. This redistribution matrix corrects a dose deposited in a column of water to match the dose that would be deposited by ray-tracing through a column of inhomogeneous tissue. The (nonzero) values of R can be derived, e.g., from the Hounsfield radiodensity values associated with computer-aided tomography density readings. FIG. 0 illustrates.

Because the dose deposition A and redistribution R are linear and can be combined to give the correct heterogeneous-tissue dose RAw. Note that the redistribution is many-to-many, i.e., the irradiation values from several contiguous voxels in the initial dose calculation Aw grid may be linearly combined to obtain the total radiation absorbed by single voxel of bone or very dense tissue the heterogeneity-corrected dose RAw. Similarly, irradiation in a single voxel in Aw can be distributed to many low-density voxels in RAw.

Notably, the redistribution matrix R is sparse and highly compressible, i.e., for each voxel $v_i$ in RAw, one embodiment determines the shallowest and deepest voxels contributing voxels in Aw and the fractions of their irradiations contributed to $v_i$. Consequently, in one embodiment, the redistribution matrix R can be represented with only four nonzero values per row providing an efficient storage and use by the GPU. For other kinds of radiation sources, the redistribution matrix may not be as sparse. In those cases, some embodiments express the redistribution as a piecewise linear function, such that the texture-mapping functions of the GPU can be utilized.

Diverging Beams

The mathematically idealized dose calculation assumes that all beams are parallel; in reality, all beams radiate from a common focal point. To handle this, some embodiments based on a recognition that a Euclidean space can always be warped so that all lines parallel to one axis meet at the focal point. Similarly, there is a counter-warp that inverts this warp (except at the focal point, which is a singularity).

Figure 7:
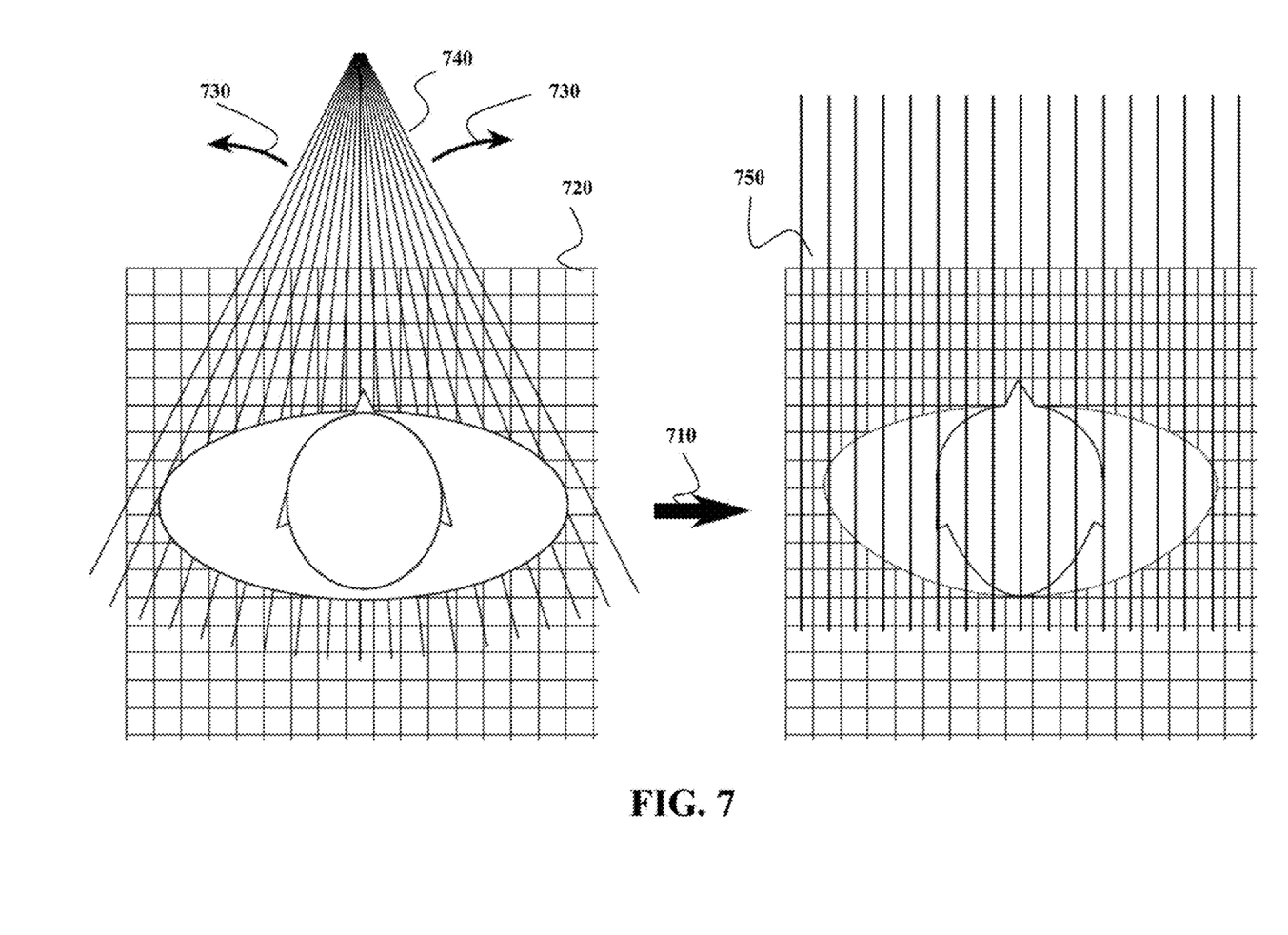
FIG. 7 is a schematic of a method for correcting the assumption of a parallel distribution of the collimated beams according to one embodiment of the invention.

FIG. 7 shows a schematic of a method for correcting the assumption of a parallel distribution of the collimated beams according to one embodiment of the invention. Specifically, the embodiment counter-warp 710 the patient geometry 720 and tissue density data. Then dose deposition and redistribution proceeds as above. The counter-warping transforms 730 the diverging beam 740 into the parallel beams 750 used to determine the approximation 315.

The counter-warping is reversed after the radiation dose is determined and the planning volume is warped back to its original geometry. In some embodiments, the warp and counter-warp operation change the volume of any subvolume of the volume but do not change the stopping power or cumulative radiation in that volume. In addition, the counter-warp can also be applied to the beam-spreading profiles to keep the geometry of the beams consistent with the geometry of the volume. Again, the warp and counter-warp are linear operators that can be handled by native GPU operations or represented by a very sparse matrix that can be combined (or sequenced) with the rotation and heterogeneous tissue redistribution matrices.

Rotated Beams and Multiport

The same technique can be used to calculate the dose from beams that are not aligned with the Z-axis of the treatment planning volume, as is the case for multiport planning. Consider a two-port case, where the beams from the first port travel parallel to the Z axis of the treatment planning volume, and the beams of the second port travel along some other axis specified by a set of rotations, for example Euler angles (azimuth, elevation, twist). In this case, some embodiments pre-determine a rotation matrix that redistributes the dose in each voxel of the original axis-aligned volume to the appropriate voxels in a counter-rotated volume. For example, one embodiment overlies the original volume and the counter-rotated volume, such that for each voxel in the original volume, its fraction is overlap with each voxel in the counter-rotated volume. This approach produces another sparse matrix P with a small number of non-zeros per row that is easily handled by the GPU. In fact, this is exactly how GPUs do rotation in volume visualization. Because rotation is linear, the rotation can be combined with the redistribution operator for heterogeneous tissue.

For multiport optimizations, an independent rotation $P_k$, redistribution $R_k$, beam basis $A_k$, and set of beam weights $w_k$ are associated with each port, yielding a cumulative all-ports dose of $\Sigma_k P_k R_k A_k w_k$. However, the Lagrange multipliers are shared between all ports, because all ports cooperate to satisfy the constraints.

Beam Absorption in Front of the Treatment Planning Volume (TPV)

The planning volume can represent the interior of the patient, but the beams are attenuated by the air, skin, tissues, and other media that lie between the planning volume and the beam source. The effect of these media on the beams can be modeled in dose optimization through the dose redistribution matrix R. For example, one embodiment adds a special layer of voxels between the TPV and the beam nozzle. The dose-volume equivalent stopping power of each voxel in this layer is set to the cumulative dose-volume stopping equivalent of all the media on the line between that voxel and the nozzle. Then the R matrix is formed as before. If there are no constraints on these special voxels, the corresponding rows of the R matrix can be dropped in the optimization.

Example

Figure 8A:
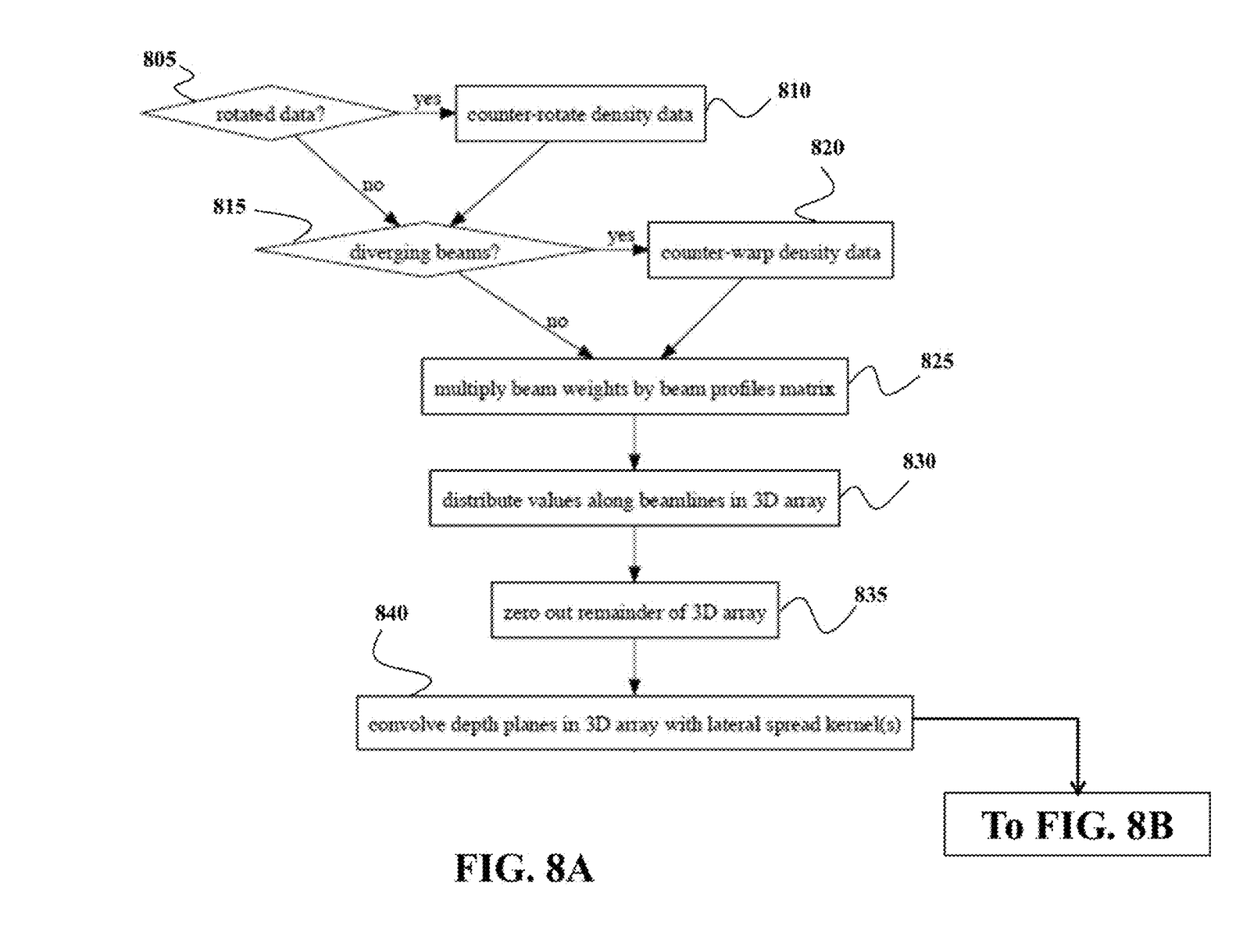
FIGS. 8A and 8B are flow charts for an exemplar method for determining a cumulative voxel radiation dose for radiation therapy treatment of the volume of the patient according to one embodiment of the invention.
Figure 8B:
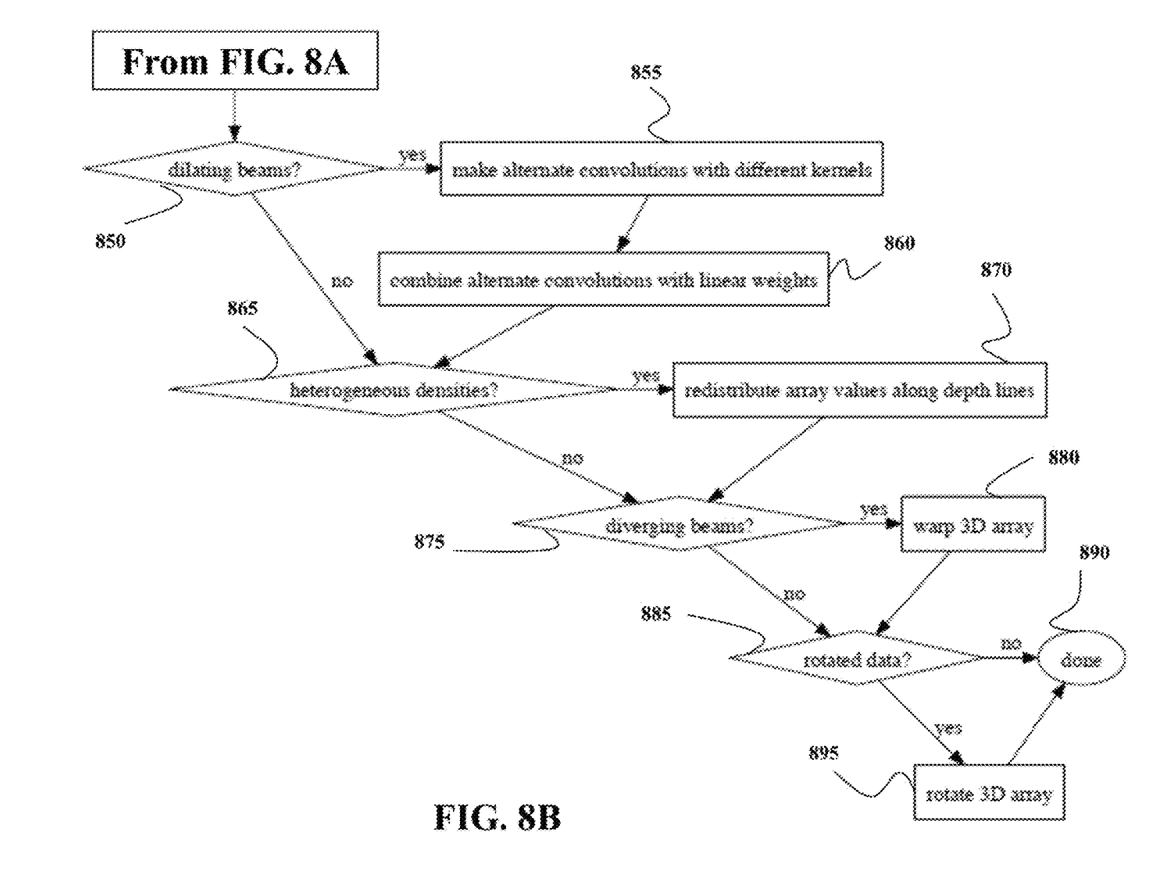

FIGS. 8A and 8B show a flow chart of an exemplar method for determining a cumulative voxel radiation dose for radiation therapy treatment of the volume of the patient. The method tests 805 if the data representing density of the volume of the patient needs to be rotated. For example, if the radiation treatment system 103 includes multiple source of power, the data is counter-rotated 810. Similarly, if the pencil beams of radiation are diverging 815, the density data are counter-wrapped 820 as described above.

The radiation deposited at each depth by each set of coaxial beams is determined 825 by multiplying the beam profile matrix by a matrix of beam weights. These deposition values are seeded 830 into the voxels along each beam line in the 3D voxel array. The rest of the 3D voxel array is zeroed 835 and the axial deposition values are spread throughout the volume 840 via planar convolutions with the lateral spread kernels. If the beams are known to dilate 850, steps 825-840 are repeated with slightly different beam profile matrices 855 and the results are linearly combined 860 to finely approximate the true radiation deposition pattern. If the density of the patient is known 865, e.g., through a CT scan, then the deposited values are redistributed up and down the 3D volume 870 to model the varied stopping power of heterogeneous tissue. Finally, any compensation for diverging beams 875 is inverted 880 and similarly any compensation for patient rotation 885 is inverted 890 to restore the patient volume to its original geometry.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component. Though, a processor may be implemented using circuitry in any suitable format. The processor can be connected to memory, transceiver, and input/output interfaces as known in the art.

Also, the various methods or processes outlined herein may be coded as software that is executable on one or more processors that employ any one of a variety of operating systems or platforms. Alternatively or additionally, the invention may be embodied as a computer readable medium other than a computer-readable storage medium, such as signals.

The terms "program" or "software" are used herein in a generic sense to refer to any type of computer code or set of computer-executable instructions that can be employed to program a computer or other processor to implement various aspects of the present invention as discussed above.

Use of ordinal terms such as "first," "second," in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Although the invention has been described with reference to certain preferred embodiments, it is to be understood that various other adaptations and modifications can be made within the spirit and scope of the invention. Therefore, it is the object of the append claims to cover all such variations and modifications as come within the true spirit and scope of the invention.

I claim:

1. A method for planning a radiation therapy treatment of a body represented by a volume of voxels, comprising:
    determining a radiation dose matrix representing a spatial distribution of a radiation dose of beams of radiation irradiating the volume with homogeneous stopping power, wherein the beams are collimated and are shifted copies of each other at each depth of the volume, wherein the spatial distribution is determined by calculating cumulative beam-axial doses in a single matrix-matrix multiplication and redistributing the cumulative beam-axial doses to all voxels in the volume using a convolution; and
    applying a set of correcting operations to the radiation dose matrix to produce a cumulative voxel radiation dose of the volume, wherein each correcting operation is linear, independent from another correcting operation and has a transform, wherein steps of the method are performed by at least one processor.

2. The method of claim 1, wherein the determining comprises:
    multiplying a vector representing weights of the beams by a matrix representing energy profiles of the beams to estimate values of a total radiation at each depth of each beam;
    substituting values in an zeroed 3D array representing the voxels in the volume with corresponding values of the total radiation; and
    convolving each depth plane in the volume with a spreading kernel.

3. The method of claim 1, wherein the determining comprises:
    determining the radiation dose matrix as a matrix-vector products Aw of a fluence matrix A representing relative intensity of radiation delivered to each voxel in the volume by each beam and a vector of nonnegative beam weights w representing time of radiation of each beam of radiation according to $Aw = \text{vec}(B^T \text{mat}(w)(N \otimes N))$, wherein N be a matrix in which each column is a spatially shifted copy of values of lateral distribution, B is a matrix of spatially shifted energy profiles, such that each column in the matrix B includes an energy profile for the beams in the same depth, wherein $\otimes$ is a Kronecker product of matrices, a function vec(•) vectorizes its argument, and a function mat(•) reshapes its argument into a matrix that conforms with its left and right multiplicands, and wherein T is a transpose operator.

4. The method of claim 1, wherein the set of correcting operations includes an operation for correcting a uniformity of a lateral distribution of energy of each beam at each depth, comprising:
    convolving each row of the radiation dose matrix to determine the multiplication ($N \otimes N$), wherein the convolving includes a first convolution with a first vector in a first lateral direction, followed by a second convolution with a second vector in a second lateral direction orthogonal to the first lateral direction.

5. The method of claim 4, wherein the convolving is according to $$\sum_j \left( \sum_i w_i v_j(z) B_i(z) \right) \cdot N((x, y), \sigma_j^2),$$

wherein $w_i$ is the weight on the ith beam, $B_i(z)$ is an integral of an energy profile at a depth z, and $N((x, y), \sigma_i^2(z))$ is a 2D Gaussian field of variance $\sigma_i^2(z)$ centered at an axis (x, y), an $v_j$ is a spreading kernel in a set J predetermined for the depth z.

6. The method of claim 1, wherein the set of correcting operations includes an operation for correcting an assumption of the homogeneous stopping power, further comprising:
    stretching each voxel in proportion to the stopping power of corresponding tissue of the volume to produce a stretched grid;
    determining a redistribution matrix R that linearly maps irradiation values deposited into a regular grid to values deposited into the stretched grid; and
    multiplying the redistribution matrix R with the radiation dose matrix.

7. The method of claim 1, wherein the set of correcting operations includes an operation for correcting an assumption of a parallel distribution of the collimated beams, further comprising:
    counter-warping a Euclidean space of tissue density data of the volume before determining the radiation dose; and
    reversing the counter-warping after determining the radiation dose.

8. The method of claim 1, wherein the set of correcting operations includes an operation for correcting multi-port propagation of the beams of radiation using a rotation of the volume with respect to, further comprising:
    counter-rotating the volume to align a grid of the volume with a port to produce a counter-rotated volume;
    determining a rotation matrix to redistribute the radiation dose in each voxel of the volume to corresponding voxels in the counter-rotated volume; and
    summing the radiation dose of the corresponding voxels of the volume and the counter-rotated volume.

9. The method of claim 1, further comprising:
    adding to the volume a proximal layer of voxels with a stopping power equivalent to a cumulative stopping power of media between a source of the beams and the body.

10. The method of claim 1, further comprising:
    performing transform operations to the cumulative voxel radiation dose of the volume in an order reversed from an order of operations determining the cumulative voxel radiation dose.

11. A method for planning a radiation therapy treatment of a body represented by a volume of voxels, comprising:

determining a radiation dose matrix representing a spatial distribution of a radiation dose of a regular 3D grid of beams irradiating the volume with homogeneous stopping power; and applying a set of correcting operations to the radiation dose matrix to produce a cumulative voxel radiation dose of the volume, wherein the set of correcting operation includes one or combination of an operation for correcting an assumption of uniformity of lateral distribution of energy of each collimated beam, an operation for correcting an assumption of the homogeneous stopping power of the volume, an operation for correcting an assumption of a parallel distribution of the collimated beams, an operation for correcting an assumption of a multi-port propagation of the collimated beams, and an operation for correcting an assumption for a cumulative stopping power of media between a beam source and the patient, wherein each correcting operation is linear, independent from another correcting operation and has a transform, and wherein steps of the method are performed by a parallel processor.

12. A radiation therapy system comprising a parallel processor for determining an approximation of a radiation dose matrix representing a spatial distribution of a radiation dose of beams of radiation irradiating a body represented by a volume of voxels, wherein the spatial distribution is determined by calculating cumulative beam-axial doses in a single matrix-matrix multiplication and redistributing the cumulative beam-axial doses to all voxels in the volume using a convolution, and for correcting the approximation using a set of linear correcting operations.

* * * * *